United States Patent [19]

Riondel et al.

[11] Patent Number: 5,498,723
[45] Date of Patent: Mar. 12, 1996

[54] PROCESS FOR THE PREPARATION OF ALKYLIMIDAZOLIDONE (METH)-ACRYLATES

[75] Inventors: Alain Riondel, Forbach; Gilles Herbst, Spicheren; Marc Esch, Freyming-Merlebach, all of France

[73] Assignee: Elf Atochem S.A., Puteaux, France

[21] Appl. No.: 329,964

[22] Filed: Oct. 27, 1994

[30] Foreign Application Priority Data

Oct. 27, 1993 [FR] France .................... 93 12833

[51] Int. Cl.$^6$ .............. C07D 233/32; C07D 233/70; C07D 233/04
[52] U.S. Cl. .............................. 548/324.1
[58] Field of Search ........................... 548/324.1

[56] References Cited

U.S. PATENT DOCUMENTS

| | | | |
|---|---|---|---|
| 2,727,016 | 12/1955 | Hankins et al. | 548/324.1 X |
| 2,831,833 | 4/1958 | Aycock et al. | 548/324.1 X |
| 2,871,223 | 1/1959 | Hankins et al. | 260/70 |
| 2,881,171 | 4/1958 | Hankins et al. | 548/324.1 X |
| 3,356,653 | 12/1967 | Sekmakas | 548/324.1 X |
| 3,356,654 | 12/1967 | Sekmakas | 548/324.1 X |
| 3,356,655 | 12/1967 | Sekmakas | 548/324.1 X |
| 4,330,550 | 5/1982 | Lautenschlager et al. | 424/273 R |
| 4,777,265 | 10/1988 | Merger et al. | 548/324.1 |
| 4,845,233 | 7/1989 | Higuchi et al. | 548/324.1 |
| 4,868,313 | 9/1989 | Pinza et al. | 548/544 |
| 5,210,199 | 5/1993 | Grosius et al. | 548/324.1 |

FOREIGN PATENT DOCUMENTS 0236994 9/1987 European Pat. Off. ..
0433135 6/1991 European Pat. Off. ..

*Primary Examiner*—Floyd D. Higel
*Attorney, Agent, or Firm*—Millen, White, Zelano, & Branigan

[57] ABSTRACT

A compound (I) is prepared by reacting at least one (meth) acrylate (II) with a heterocyclic alcohol (III), in the presence of at least one catalyst chosen from magnesium alkoxides $Mg(OR)_2$.

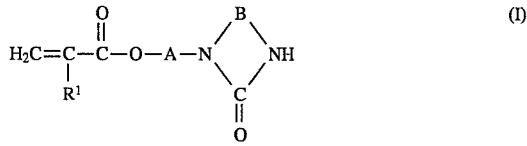

(I)

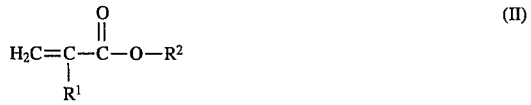

(II)

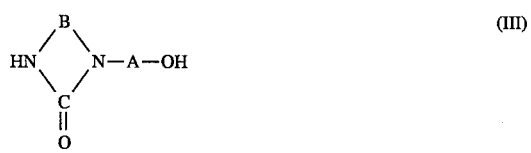

(III)

$R=C_1-C_4$ alkyl. $R^1=H, CH_3$; A, B=straight or branched $C_2-C_5$ hydrocarbon chain; $R^2=C_1-C_4$ alkyl.

14 Claims, No Drawings

PROCESS FOR THE PREPARATION OF ALKYLIMIDAZOLIDONE (METH)-ACRYLATES

The present invention relates to a process for the production of a compound of formula:

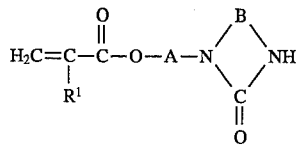 (I)

in which:
$R^1$ represents hydrogen or methyl; and
A and B each independently represent a straight or branched hydrocarbon chain having from 2 to 5 carbon atoms,
by reaction of at least one (meth)acrylate of formula:

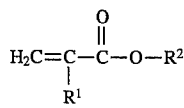 (II)

in which:
$R^1$ has the above meaning; and
$R^2$ represents a $C_1$–$C_4$ alkyl group,
with a heterocyclic alcohol of formula:

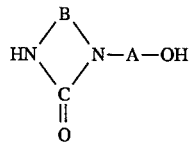 (III)

in which A and B have the above meanings.

These compounds of formula (I) are known for their role in the constitution of polymers which are useful as coatings and adhesives, for treating paper and textiles, in particular by American Patent U.S. Pat. No. 2,871,223, as well as for their uses as leather-treating agents, and in the production of emulsion paints. Ethylimidazolidone methacrylate (EIOM) is mainly used in paints and as a moist-adhesion promoter.

In the process defined above, known by the European Patent Application EP-A-0 236 994, the catalysts are chosen from titanium alkoxides, for example tetraalkyl titanates, and the chelates of Ti, Zr, Fe or Zn with 1,3-dicarbonyl compounds, for instance the acetylacetonates of Ti, Zr, Fe or Zn.

It may also be pointed out that, in this European Application EP-A-0 236 994, the known use of basic KOH, $K_2CO_3$ and NaOMe catalysts and basic catalysts derived from pyrimidine is reported, with the recommendation that they should not be used on account of their strong tendency to promote side reactions.

It is also known, from European Patent Application EP-A-0 433 135, to use dialkyltin oxides, dialkyltin dialkoxides and dialkyltin diesters as catalysts for this same reaction. Di-n-butyltin oxide (DBTO) is mentioned, among others.

However, in the case of the synthesis of EIOM, it has been sought to achieve the greatest possible conversion of hydroxyethylimidazolidone (HEIO), which, in the case of catalysis by DBTO, requires a high level of temperature.

A different type of catalyst, allowing in particular good production efficiency and good selectivity at lower reaction temperatures to be obtained, has thus been sought. It has now been surprisingly discovered that the use of a magnesium alkoxide makes it possible to work at a temperature below 100° C. (95° C.–96° C. in particular), while at the same time leading to good results from the point of view of the yield of EIOM and of the conversion of HEIO.

The subject of the present invention is thus the process for the production of a compound of formula (I) as has been described above, in the presence of at least one magnesium alkoxide as catalyst.

Examples of magnesium alkoxides $Mg(OR)_2$ which may be mentioned are those for which R represents a linear $C_1$–$C_4$ alkyl group, such as methyl, ethyl, n-propyl and n-butyl. The alkoxides for which R represents ethyl or n-propyl may be mentioned more particularly.

It is preferred to use magnesium diethoxide.

Examples of reactants of formula (II) which may be mentioned in particular are the methyl, ethyl, n-propyl, n-butyl and isobutyl acrylates and methacrylates.

1-(2-Hydroxyethyl)-2-imidazolidone (HEIO) may in particular be mentioned as an example of a heterocyclic alcohol of formula (III).

The amount of catalyst used for implementation of the process according to the invention is generally between 0.5 and 4 mol % approximately and preferably between 1 and 2.5 mol % approximately relative to the heterocyclic alcohol of formula (III).

The reaction of the process according to the invention may be carried out in the presence of an excess of one or other of the reactants. It is, however, advisable for the (meth)acrylate of formula (II)/heterocyclic alcohol of formula (III) molar ratio to be between 1.1 and 7.0 approximately, preferably between 2.0 and 6.0. By working with a large molar excess of (meth)acrylate relative to the heterocyclic alcohol, a solution of compound of formula (I) in (meth)acrylate is obtained on conclusion of the reaction, which solution may be used directly for certain applications, such as for obtaining paints and coatings or alternatively for treating leather.

The reaction of the process according to the invention is preferably carried out in the presence of at least one polymerization inhibitor used, for example, in an amount of 0.05 to 0.5% by weight based on the weight of the heterocyclic alcohol of formula (III). As examples of polymerization inhibitors which may be used there may in particular be mentioned phenothiazine, hydroquinone methyl ether, di-tert-butylcatechol, hydroquinone, p-anilinophenol, para-phenylenediamine and their mixtures in all proportions.

The reaction of the process according to the invention is preferably carried out at a pressure not exceeding atmospheric pressure, for example a pressure between 0.3 and 1 bar. The reaction is advantageously performed with air bubbled through, in order to improve the efficiency of the stabilizers. It is carried out by mixing the (meth)acrylate of formula (II) and the heterocyclic alcohol of formula (III), and by heating the reaction mixture to reflux, generally at a temperature between 85° and 105° C., this temperature obviously depending on the exact nature of the alcohol and of the (meth)acrylate, and on the catalytic system used.

In the implementation of the process according to the invention, it is advisable to achieve maximum dehydration before addition of the catalyst, so as to avoid deactivation of the latter by water. This result may, for example, be achieved by heating the initial mixture of (meth)acrylate of formula (II), heterocyclic alcohol of formula (III) and polymerization inhibitor to reflux, while separating out by distillation the azeotrope of (meth)acrylate and water when an azeotrope of methacrylate and water forms. At this stage, after separation of the distillate, the catalyst is introduced into the hot reaction mixture.

The duration of the reaction according to the invention obviously depends on the reaction conditions, such as the temperature, the pressure and the amount of catalyst used, but is generally between 3 and 15 hours approximately. It obviously also depends on the nature of the reactants used.

The reaction mixture is thus heated to reflux until the head temperature reaches the temperature of distillation of the azeotrope of (meth)acrylate and alcohol of formula $R_2OH$ formed by the reaction when an azeotrope forms.

The possible excess (meth)acrylate may subsequently be removed by evaporation, in order to isolate the compound of formula (I) from the reaction medium, generally in the solid state: thus, 1-(2-hydroxyethyl)-2-imidazolidone acrylate is a white crystalline solid of melting point equal to 43° C., which is soluble under cold conditions in ketones, alcohols, aromatic hydrocarbons and water, insoluble under cold conditions in saturated hydrocarbons and which precipitates at 0° C. in ethyl acrylate. 1-(2-Hydroxy-ethyl)-2-imidazolidone methacrylate is a white crystalline solid of melting point equal to 47° C., having the same solubility properties as the above acrylate. On conclusion of the evaporation step, the crystalline solid product may in addition be purified by filtration, followed by washing with petroleum ether, and drying.

Isolation of the compound (I) may also be performed by partial evaporation of the (meth)acrylate, followed by crystallization at a sufficiently low temperature (preferably lower than or equal to 0° C.) and for a sufficiently long period (which may be up to 15 hours) and then filtration, followed by the purification steps described above.

Finally, a third method for isolating the compound of formula (I) from the solution containing it consists in carrying out an extraction with water, followed by separation of the phases after settling has taken place, concentration of the (meth)acrylate and the purification steps described above.

The examples which follow illustrate the invention without, however, implying any limitation thereof. In these examples, the percentages are indicated by weight except where otherwise indicated.

EXAMPLE

Example 1

195 g of HEIO and 565 g of methyl methacrylate (MMA), along with 0.36 g of phenothiazine (PTZ) as stabilizing agent, are introduced into a jacketed glass reactor equipped with a temperature measuring probe, a variable-speed mechanical stirrer and a packed adiabatic column surmounted with a reflux-head. The column head is stabilized with a 0.2% solution of hydroquinone methyl ether (HQME) in MMA. The contents of the reactor are brought to boiling at atmospheric pressure for 1 hour, at a column head temperature of 98°–100° C. and at a column foot temperature lower than or equal to 100° C., and the water is removed by azeotropic distillation with the methyl methacrylate.

3.4 g of magnesium ethoxide and MMA are subsequently introduced into the reactor, taking care that the MMA/HEIO molar ratio is equal to 3.5 (after drying). The pressure is adjusted in order to maintain a temperature T of 96° C. in the reactor. Withdrawal of the MMA/MeOH azeotrope is regulated by a set temperature at the column head (equal to 65° C.). When the amount of methanol withdrawn corresponds to the expected amount, the reaction is continued until no further formation of methanol is observed (column head temperature=boiling point of MMA), at full reflux and at the pressure in question.

After cooling, the crude EIOM is recovered.

The yield of EIOM and the conversion of HEIO are determined by liquid phase chromatography (HPLC) analysis of the reaction crude, using the following equations:

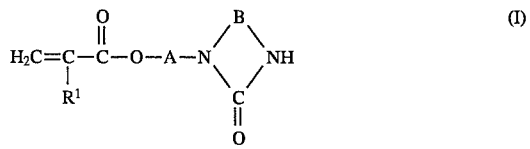

The results are reported in the table below, which also includes the data and results from four other examples.

TABLE

| Ex. | Molar ratio [MMA]/[HEIO] | HPLC analysis of the crude mixture obtained (%) | | | T (°C.) | Y (%) | C (%) |
|---|---|---|---|---|---|---|---|
| | | MMA | HEIO | EIOM | | | |
| 1 | 3.5 | 44.1 | 0.7 | 42.2 | 96 | 80 | 97 |
| 2 | 5.2 | 64.2 | 0.68 | 34.6 | 96 | 87 | 97.2 |
| 3* | 5.2 | 57.5 | 0.42 | 33.3 | 96 | 85 | 97.7 |
| 4 | 3.5 | 45.2 | 4.6 | 40.3 | 90 | 74.5 | 87 |
| 5 | 2.7 | 40.5 | 1.4 | 46.9 | 96 | 77.8 | 96.5 |

*The catalyst used in this example is magnesium propoxide (the catalyst used in Examples 2, 4 and 5 is the same as that in Example 1).

We claim:

1. A process for the production of a compound of formula:

in which:

$R^1$ represents hydrogen or methyl; and

A and B each independently represent a straight or branched hydrocarbon chain having from 2 to 5 carbon atoms, by reaction of at least one (meth)acrylate of formula:

$$H_2C=C(R^1)-C(=O)-O-R^2 \quad \text{(II)}$$

in which:

$R^1$ has the above meaning; and $R^2$ represents a $C_1$–$C_4$ alkyl group, with a heterocyclic alcohol of formula:

$$\underset{HN}{\overset{B}{\diagup\diagdown}}\underset{\diagdown\diagup}{N-A-OH} \quad \text{(III)}$$
$$\underset{C}{\overset{}{}}$$
$$\underset{O}{\overset{\|}{}}$$

in which A and B have the above meanings, in the presence of a catalytic quantity of at least one magnesium alkoxide.

2. A process according to claim 1, wherein the magnesium alkoxide is of the formula $Mg(OR)_2$, R representing $C_1$–$C_4$-alkyl.

3. A process according to claim 2, wherein R represents ethyl or n-propyl.

4. A process according to claim 1, wherein the catalyst is used in an amount of 0.5 to 4 mol % relative to the heterocyclic alcohol of formula (III).

5. A process according to claim 1, wherein the reaction is carried out at a temperature between 85° and 105° C.

6. A process according to claim 1, wherein the molar ratio of the (meth)acrylate of formula (II) to the heterocyclic alcohol of formula (III) which is between 1.1 and 7.0 is used.

7. A process according to claim 1, wherein the reaction is carried out for a period of between 3 and 15 hours and at a pressure not exceeding atmospheric pressure.

8. A process according to claim 1, wherein the reaction is carried out in the presence of at least one polymerization inhibitor chosen from the group consisting of phenothiazine, hydroquinone methyl ether, di-tert-butylcatechol, hydroquinone, p-anilinophenol, paraphenylenediamine and mixtures thereof.

9. A process according to claim 2, wherein the catalyst is used in an amount of 0.5 to 4 mol % relative to the heterocyclic alcohol of formula (III).

10. A process according to claim 3, wherein the catalyst is used in an amount of 0.5 to 4 mol % relative to the heterocyclic alcohol of formula (III).

11. A process according to claim 9, wherein the reaction is carried out at a temperature between 85° and 105° C.

12. A process according to claim 10, wherein the reaction is carried out at a temperature between 85° and 105° C.

13. A process according to claim 11, wherein the reaction is carried out for a period of between 3 and 15 hours and at a pressure not exceeding atmospheric pressure.

14. A process according to claim 12, wherein the reaction is carried out in the presence of at least one polymerization inhibitor chosen from the group consisting of phenothiazine, hydroquinone methyl ether, di-tert-butylcatechol, hydroquinone, p-anilinophenol, paraphenylenediamine and mixtures thereof.

* * * * *